US011125759B2

(12) United States Patent
Jessen et al.

(10) Patent No.: US 11,125,759 B2
(45) Date of Patent: Sep. 21, 2021

(54) COMPOSITIONS AND METHODS TO DETECT NON-COELIAC GLUTEN SENSITIVITY

(71) Applicant: Laboratory Corporation of America Holdings, Burlington, NC (US)

(72) Inventors: Walter Joseph Jessen, New Palestine, IN (US); Alexander L. Katayev, Graham, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 337 days.

(21) Appl. No.: 15/977,173

(22) Filed: May 11, 2018

(65) Prior Publication Data

US 2018/0328946 A1    Nov. 15, 2018

Related U.S. Application Data

(60) Provisional application No. 62/505,378, filed on May 12, 2017.

(51) Int. Cl.
*G01N 33/68* (2006.01)

(52) U.S. Cl.
CPC ..... *G01N 33/6893* (2013.01); *G01N 33/6854* (2013.01); *G01N 33/6863* (2013.01); *G01N 33/6869* (2013.01); *G01N 2333/525* (2013.01); *G01N 2333/54* (2013.01); *G01N 2333/5421* (2013.01); *G01N 2333/5428* (2013.01); *G01N 2800/06* (2013.01); *G01N 2800/065* (2013.01); *G01N 2800/60* (2013.01)

(58) Field of Classification Search
CPC ........... G01N 33/6893; G01N 33/6863; G01N 33/6869; G01N 33/6854; G01N 2333/5428; G01N 2333/5421; G01N 2333/525; G01N 2800/06
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 5,846,710 A | 12/1998 | Bajaj |
| 5,885,775 A | 3/1999 | Haff et al. |
| 5,888,819 A | 3/1999 | Goelet et al. |
| 5,945,526 A | 8/1999 | Lee et al. |
| 6,280,947 B1 | 8/2001 | Shuber et al. |
| 6,482,595 B2 | 11/2002 | Shuber et al. |
| 6,503,718 B2 | 1/2003 | Shuber et al. |
| 6,818,395 B1 | 11/2004 | Quake et al. |
| 6,919,174 B1 | 7/2005 | Shuber |
| 7,169,560 B2 | 1/2007 | Lapidus et al. |
| 7,282,337 B1 | 10/2007 | Harris |
| 7,501,251 B2 | 3/2009 | Koester et al. |
| 2009/0156412 A1 | 6/2009 | Harris et al. |
| 2019/0204341 A1* | 7/2019 | Anderson ............. A61K 38/00 |

FOREIGN PATENT DOCUMENTS

WO    2008052185    5/2008

OTHER PUBLICATIONS

Volta Biomarkers For Non-Celiac Gluten Sensitivity: A Tough, But Intriguing Challenge For Researchers. 16th International Coeliac Disease Symposium, Jun. 21-24, Prague, Czech Republic (Jan. 1, 2003]).*
U.S. Appl. No. 62/505,536, filed May 12, 2017, Jessen et al.
U.S. Appl. No. 62/523,382, filed Jun. 22, 2017, Jessen et al.
Ausubel et al., Current Protocols in Molecular Biology, 1994, vol. 1., John Wiley & Sons, Secaucus, N.J.
Ausubel F.M., Short Protocols in Molecular Biology, Fourth Edition, Chapter 2, 1999, John Wiley & Sons, N.Y.
Bauer-Mehren et al., "Gene-Disease Network Analysis Reveals Functional Modules in Mendelian, Complex and Environmental Diseases", PLoS One vol. 6, No. 6: e20284, Jun. 2011, 13 pages.
Benjamini et al., "Controlling the False Discovery Rate: A Practical and Powerful Approach to Multiple Testing", Journal of the Royal Statistical Society. Series B (Methodological), vol. 57, No. 1, 1995, 13 pages.
Braslavsky et al., "Sequence Information can be obtained from single DNA molecules", PNAS, Apr. 1, 2003, vol. 100, No. 7, pp. 3960-3964.
Cheng et al., "Polysearch: A Web-based Text Mining System for Extracting Relationships Between Human Diseases, Genes, Mutations, Drugs and Metabolites", Nucleic Acids Research, vol. 36, 2008, pp. W399-W405.
Davis et al., "The Comparative Toxicogenomics Database's 10th year anniversary: update 2015", Nucleic Acids Research, 2015, vol. 43, Database issue, 2015, pp. D914-D920.
Dijkstra , "A Note on Two Problems in Connexion with Graphs", Numerische Mathematik, vol. 1, 1959, pp. 269-271.
Ekins et al., "Algorithms for Network Analysis in Systems—ADME/Tox using the MetaCore and Meta Drug Platforms", Xenobiotica, vol. 36, Nos. 10-11, Oct.-Nov. 2006, pp. 877-901.
Haugland, R.P., The Handbook of Fluorescent Probes and Research Products, Ninth Edition, 2002, Molecular Probes, Inc., Eugene, OR.
Hoogendorn et al., "Genotyping single nucleotide polymorphisms by primer extension and high performance liquid chromatography", Human Genetics, 1999, vol. 104, pp. 89-93.
Huang et al., "Bioinformatics Enrichment Tools: Paths Toward the Comprehensive Functional Analysis of Large Gene Lists", Nucleic Acids Research, vol. 37, No. 1, 2009, 13 pages.
Huang et al., "Systematic and Integrative Analysis of Large Gene Lists Using David Bioinformatics Resources", Nature Protocols, vol. 4, No. 1, 2009, 43 pages.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85 pp. 5879-5883.

(Continued)

*Primary Examiner* — Gailene Gabel
(74) *Attorney, Agent, or Firm* — Kilpatrick Townsend & Stockton LLP

(57) ABSTRACT

Disclosed are compositions and methods to detect proteins associated with non-coeliac gluten sensitivity (NCGS). Such markers may be useful to allow individuals susceptible to NCGS to manage their food intake to avoid symptoms and further progression of disease.

22 Claims, 1 Drawing Sheet

(56) References Cited

OTHER PUBLICATIONS

Jessen et al., "Mining PubMed for Biomarker-Disease Associations to Guide Discovery", Nature Precedings Pre-Publication Research and Preliminary Findings, Available online at http://precedings.nature.com/documents/6941/version/1, Feb. 26, 2012, 1 page.
Ju et al., "Fluorescence energy transfer dye-labeled primers for DNA sequencing and analysis", Proc. Natl. Acad. Sci. USA, May 1995, vol. 92, pp. 4347-4351.
Maxam et al., "A new method for sequencing DNA", Proc. Natl. Sci. USA, Feb. 1977, vol. 74, No. 2, pp. 560-564.
Needleman et al., "A General Method Applicable to the Search for Similarities in the Amino Acid Sequence of Two Proteins", J. Mol. Bio., 1970, vol. 48, pp. 443-453.
Newton et al., "Analysis of any point mutation in DNA. The amplification refractory mutation system (ARMS)", Nucleic Acid Research, 1989, vol. 17, No. 7, pp. 2503-2516.
Nickerson et al., "Automated DNA diagnostics using an ELISA-based oligonucleotide ligation assay", Proc. Natl. Acad. Sci. USA, 1990, vol. 87, pp. 8923-8927.
Okayama et al., "Rapid, nonradioactive detection of mutations in the human genome by allele-specific amplification", J. Lab. Clin. Med., Aug. 1989, vol. 114, No. 2. pp. 105-113.
Paul et al., Fundamental Immunology Third Edition, 1993.
PCT/US2018/032223 , "International Search Report and Written Opinion", dated Aug. 21, 2018, 15 pages.
PCT/US2018/032223 , "Invitation to Pay Additional Fees and Partial Search Report", dated Jun. 27, 2018, 10 pages.
Pearson et al., "Improved tools for biological sequence comparison", Proc. Natl. Acad. Sci. USA, Apr. 1988, vol. 95, pp. 2444-2448.
Piggee et al., "Capillary Electrophoresis for the detection of known point mutations by single-nucleotide extension and laser-induced fluorescence detection", Journal of Chromatography A, 1997, vol. 781, pp. 367-375.
Pinero et al., "DisGeNET: A Discovery Platform for the Dynamical Exploration of Human Diseases and Their Genes", Database (Oxford), vol. 2015, Article ID bav028, 17 pages, 2015.
Poddar S.K., "Symmetric vs asymmetric PCR and molecular beacon probe in the detection of a target gene of adenovirus", Molecular and Cellular Probes, 2000, vol. 14, pp. 25-32.
Sambrook et al., Molecular Cloning: A Laboratory Manual, Second Edition, 1989, Cold Spring Harbor Press, Plainview, N.Y.
Sanger et al., "DNA sequencing with chain-terminating inhibitors", Proc. Natl. Acad. Sci. USA, Biochemistry, Dec. 1977, vol. 74, No. 12, pp. 5463-5467.
Sarkar et al., "Characterization of Polymerase Chain Reaction Amplification of Specifics Alleles", Analytical Biochemistry, 1990, vol. 186, pp. 64-68.
Smith et al., "Comparison of Biosequences", Advances in Applied Mathematics, 1981, vol. 2, pp. 482-489.
Uhde et al., "Intestinal Cell Damage and Systemic Immune Activation in Individuals Reporting Sensitivity to Wheat in the Absence of Coeliac Disease", vol. 65, No. 12, Available Online At: http://gut.bmj.com/, 2016, pp. 1-8.
Volta , "Biomarkers for Non-Celiac Gluten Sensitivity: A Tough, But Intriguing Challenge for Researchers", 16th International Coeliac Disease Symposium, Jun. 21-24, Prague, Czech Republic, Jan. 1, 2003, 18 pages.
Wilbur et al., "Rapid similarity searches of nucleic acid and protein data banks", Proc. Natl. Acad. Sci. USA., Feb. 1983, vol. 80, pp. 726-730.
Wu et al., "Allele-specific enzymatic amplification of B-globin genomic DNA for diagnosis of sickle cell anemia", Proc. Natl. Acad. Sci. USA, Apr. 1989, vol. 86, pp. 2757-2760.
CA 3,057,421, Office Action, dated Dec. 30, 2020, 6 pages.
Volta, U. et al., "Non-Celiac Gluten Sensitivity: Questions Still to Be Answered Despite Increasing Awareness", Cellular & Molecular Immunology 10:393-392 (20 vol. 10, 2013, pp. 383-392.
Volta, U. et al., "Non-Coeliac Gluten/Wheat Sensitivity: Advances in Knowledge and Relevant Questions", Expert Rev. Gastroenterol. Hepatol. 11(1):9-18 (2016).

\* cited by examiner

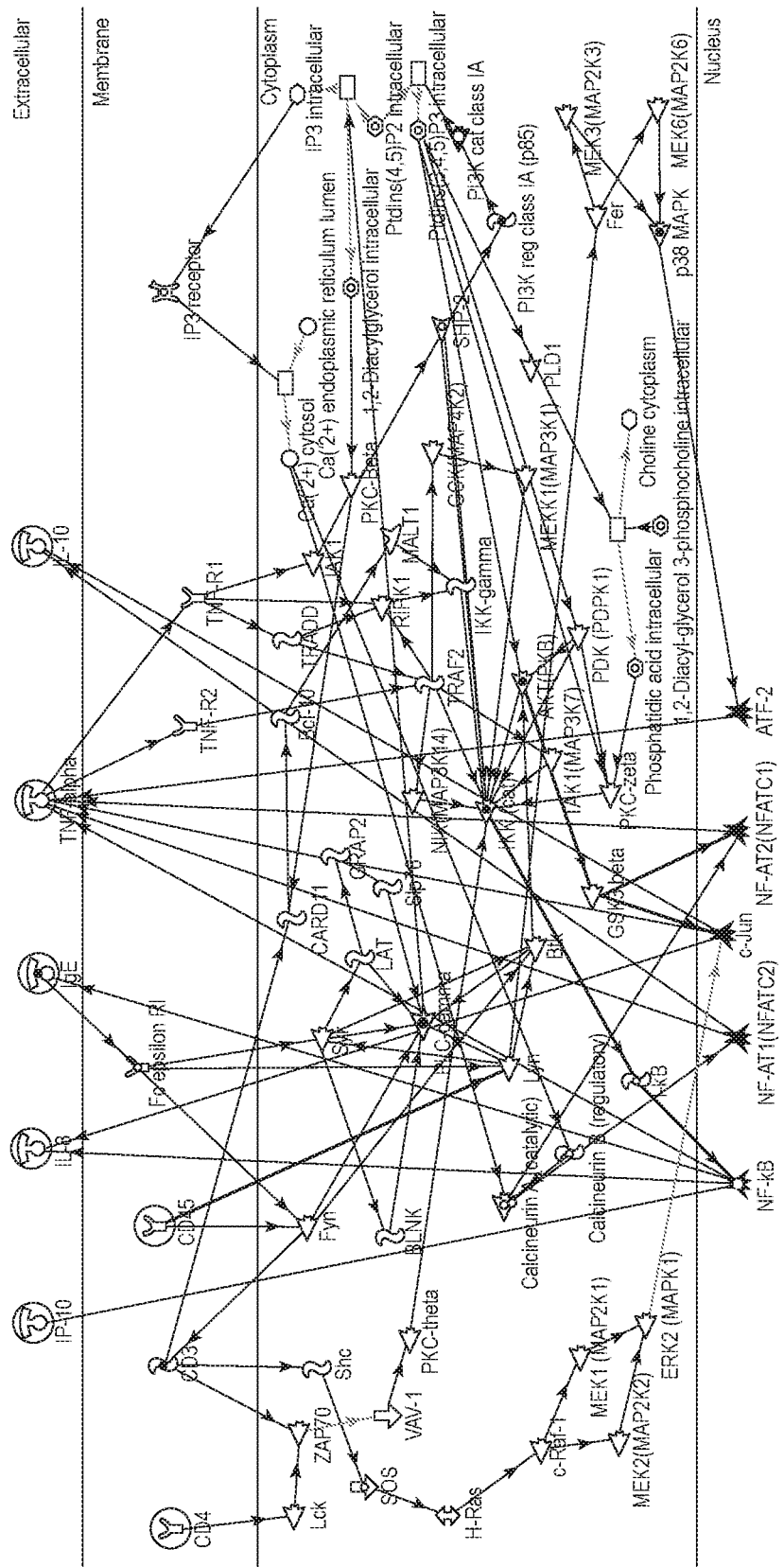

US 11,125,759 B2

COMPOSITIONS AND METHODS TO DETECT NON-COELIAC GLUTEN SENSITIVITY

RELATED APPLICATIONS

This application claims priority to U.S. Patent Application No. 62/505,378, filed May 12, 2017. The contents of U.S. Provisional Patent Application No. 62/505,378 is incorporated by reference in its entirety herein.

FIELD OF DISCLOSURE

The disclosure relates to methods and compositions for diagnosing non-coeliac gluten sensitivity.

BACKGROUND

Coeliac disease is an autoimmune disorder with genetic, environmental and immunological components. Symptoms of coeliac disease may be triggered by ingestion of wheat gluten and certain related proteins of rye and barley. Such symptoms may include inflammation, villous atrophy and crypt hyperplasia in the small intestine. There are, however, certain individuals who experience a range of symptoms in response to wheat ingestion without the characteristic serological or histological evidence of coeliac disease. The term non-coeliac gluten sensitivity (NCGS) and non-coeliac wheat sensitivity (NCWS) are generally used to refer to this condition.

The biological mechanisms behind NCGS are unknown and there are few, if any, biomarkers that provide a reliable indication of this condition. Still, it would be helpful for individuals having susceptibility to NCGS to adjust their diet so as to avoid triggering an onset of symptoms and/or promoting further progression of the disease. Thus, there is a need to develop and evaluate biomarkers for NCGS.

SUMMARY

The present disclosure may be embodied in a variety of ways.

In one embodiment, disclosed is a method to detect biomarkers associated with non-coeliac gluten sensitivity (NCGS) in an individual comprising the steps of: obtaining a sample from the individual; and measuring the amount of at least one of IL-8, IL-10, TNF-Alpha or total IgE protein in the sample.

Other features, objects, and advantages of the disclosure herein are apparent in the detailed description, drawings and claims that follow. It should be understood, however, that the detailed description, the drawings, and the claims, while indicating embodiments of the disclosed methods, compositions and systems, are given by way of illustration only, not limitation. Various changes and modifications within the scope of the invention will become apparent to those skilled in the art.

FIGURES

The disclosure may be better understood in view of the following non-limiting FIGURES.

FIG. 1 shows an example of a multi-node interaction network identifying markers associated with NCGS.

DETAILED DESCRIPTION

Terms and Definitions

In order for the disclosure to be more readily understood, certain terms are first defined. Additional definitions for the following terms and other terms are set forth throughout the specification.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "and/or" generally is used to refer to at least one or the other. In some case the term "and/or" is used interchangeably with the term "or." The term "including" is used herein to mean, and is used interchangeably with, the phrase "including but not limited to." The term "such as" is used herein to mean, and is used interchangeably with, the phrase "such as but not limited to."

Unless defined otherwise, all technical and scientific terms used herein have the same meaning as commonly understood by one of ordinary skill in the art. Practitioners are particularly directed to Current Protocols in Molecular Biology (Ausubel) for definitions and terms of the art.

Also as used herein, "at least one" contemplates any number from 1 to the entire group. For example, for a listing of four markers, the phrase at "least one" is understood to mean 1, 2, 3 or 4 markers.

Also, as used herein, "comprising" includes embodiments more particularly defined using the term "consisting of".

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present disclosure typically can be obtained by structural modification of a known peptide sequence using unnatural amino acids, conformational restraints, isosteric replacement, and the like.

Allele: As used herein, the term "allele" refers to different versions of a nucleotide sequence of a same genetic locus (e.g., a gene).

Allele specific primer extension (ASPE): As used herein, the term "allele specific primer extension (ASPE)" refers to a mutation detection method utilizing primers which hybridize to a corresponding DNA sequence and which are extended depending on the successful hybridization of the 3' terminal nucleotide of such primer. Typically, extension primers that possess a 3' terminal nucleotide which form a perfect match with the target sequence are extended to form extension products. Modified nucleotides can be incorporated into the extension product, such nucleotides effectively labeling the extension products for detection purposes. Alternatively, an extension primer may instead comprise a 3' terminal nucleotide which forms a mismatch with the target sequence. In this instance, primer extension does not occur unless the polymerase used for extension inadvertently possesses exonuclease activity.

Amplification: As used herein, the term "amplification" refers to any methods known in the art for copying a target nucleic acid, thereby increasing the number of copies of a selected nucleic acid sequence. Amplification may be exponential or linear. A target nucleic acid may be either DNA or RNA. Typically, the sequences amplified in this manner form an "amplicon." Amplification may be accomplished with various methods including, but not limited to, the polymerase chain reaction ("PCR"), transcription-based amplification, isothermal amplification, rolling circle amplification, etc. Amplification may be performed with relatively similar amount of each primer of a primer pair to generate a double stranded amplicon. However, asymmetric PCR may be used to amplify predominantly or exclusively a single stranded product as is well known in the art (e.g., Poddar et al. *Molec. And Cell. Probes* 14:25-32 (2000)). This can be achieved using each pair of primers by reducing the concentration of one primer significantly relative to the other primer of the pair (e.g., 100 fold difference). Amplification by asymmetric PCR is generally linear. A skilled artisan will understand that different amplification methods may be used together.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Also, throughout this application, the term "about" is used to indicate that a value includes the inherent variation of error for the device, the method being employed to determine the value, or the variation that exists among samples.

Associated with a syndrome or disease of interest: As used herein, "associated with a syndrome or disease of interest" means that the variant is found with in patients with the syndrome or disease of interest more than in non-syndromic or non-disease controls. Generally, the statistical significance of such association can be determined by assaying a plurality of patients.

Biological Sample and Sample: As used herein, the term "biological sample" encompasses any sample obtained from a biological source. A biological sample can, by way of non-limiting example, include blood, serum, plasma, tissue biopsty, cell-free DNA, amniotic fluid, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. The term biological sample encompasses samples which have been processed to release or otherwise make available a nucleic acid or protein for detection as described herein. For example, a biological sample may include a cDNA that has been obtained by reverse transcription of RNA from cells in a biological sample. The biological sample may be obtained from a stage of life such as a fetus, young adult, adult, and the like. Fixed or frozen tissues also may be used.

Biomarker: As used herein, the term "biomarker" refers to one or more nucleic acids, polypeptides and/or other biomolecules (e.g., cholesterol, lipids) that can be used to diagnose, or to aid in the diagnosis or prognosis of a disease or syndrome of interest, either alone or in combination with other biomarkers; monitor the progression of a disease or syndrome of interest; and/or monitor the effectiveness of a treatment for a syndrome or a disease of interest.

Binding agent: As used herein, the term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

Carrier: The term "carrier" refers to a person who is symptom-free but carries a mutation that can be passed to his/her children. Typically, for an autosomal recessive disorder, a carrier has one allele that contains a disease causing mutation and a second allele that is normal or not disease-related.

Coding sequence vs. non-coding sequence: As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom. As used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Complement: As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Conserved: As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

A "control" or "predetermined standard" for a biomarker refers to the levels of expression of the biomarker in healthy subjects or the expression levels of said biomarker in non-diseased or non-syndromic tissue from the same subject. The control or predetermined standard expression levels or amounts of protein for a given biomarker can be established by prospective and/or retrospective statistical studies using only routine experimentation. Such predetermined standard expression levels and/or protein levels (amounts) can be determined by a person having ordinary skill in the art using well known methods.

Crude: As used herein, the term "crude," when used in connection with a biological sample, refers to a sample which is in a substantially unrefined state. For example, a crude sample can be cell lysates or biopsy tissue sample. A crude sample may exist in solution or as a dry preparation.

Deletion: As used herein, the term "deletion" encompasses a mutation that removes one or more nucleotides from a naturally-occurring nucleic acid.

Disease or syndrome of interest: As used herein, a disease or syndrome of interest is NCGS. NCGS as used here includes non-coeliac wheat sensitivity (NCWS).

Detect: As used herein, the term "detect", "detected" or "detecting" includes "measure," "measured" or" measuring" and vice versa.

Detectable moiety: As used herein, the term "detectable moiety" or "detectable biomolecule" or "reporter" refers to a molecule that can be measured in a quantitative assay. For example, a detectable moiety may comprise an enzyme that may be used to convert a substrate to a product that can be measured (e.g., a visible product). Or, a detectable moiety may be a radioisotope that can be quantified. Or, a detectable moiety may be a fluorophore. Or, a detectable moiety may be a luminescent molecule. Or, other detectable molecules may be used.

Epigenetic: As used herein, an epigenetic element can change gene expression by a mechanism other than a change in the underlying DNA sequences. Such elements may include elements that regulate paramutation, imprinting, gene silencing, X chromosome inactivation, position effect, reprogramming, transvection, maternal effects, histone modification, and heterochromatin.

Epitope: As used herein, the term "epitope" refers to a fragment or portion of a molecule or a molecule compound (e.g., a polypeptide or a protein complex) that makes contact with a particular antibody or antibody like proteins.

Exon: As used herein an exon is a nucleic acid sequence that is found in mature or processed RNA after other portions of the RNA (e.g., intervening regions known as introns) have been removed by RNA splicing. As such, exon sequences generally encode for proteins or portions of proteins. An intron is the portion of the RNA that is removed from surrounding exon sequences by RNA splicing.

Expression and expressed RNA: As used herein expressed RNA is an RNA that encodes for a protein or polypeptide ("coding RNA"), and any other RNA that is transcribed but not translated ("non-coding RNA"). The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The measurement of an amount of a protein and/or the expression of a biomarker of the disclosure may be assessed by any of a wide variety of well-known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In certain embodiments, expression of a marker gene is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a protein corresponding to the marker gene, such as the protein encoded by the open reading frame corresponding to the marker gene or such a protein which has undergone all or a portion of its normal post-translational modification. In certain embodiments, a reagent may be directly or indirectly labeled with a detectable substance. The detectable substance may be, for example, selected, e.g., from a group consisting of radioisotopes, fluorescent compounds, enzymes, and enzyme co-factor. Methods of labeling antibodies are well known in the art.

In another embodiment, expression of a marker gene is assessed by preparing mRNA/cDNA (i.e. a transcribed polynucleotide) from cells in a sample, and by hybridizing the mRNA/cDNA with a reference polynucleotide which is a complement of a polynucleotide comprising the marker gene, and fragments thereof. cDNA can, optionally, be amplified using any of a variety of polymerase chain reaction methods prior to hybridization with the reference polynucleotide; preferably, it is not amplified.

Familial history: As used herein, the term "familial history" typically refers to occurrence of events (e.g., disease related disorder or mutation carrier) relating to an individual's immediate family members including parents and siblings. Family history may also include grandparents and other relatives.

Flanking: As used herein, the term "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase. For example, primers that flank mutant sequences do not actually anneal to the mutant sequence but rather anneal to sequence that adjoins the mutant sequence. In some cases, primers that flank an exon are generally designed not to anneal to the exon sequence but rather to anneal to sequence that adjoins the exon (e.g. intron sequence). However, in some cases, amplification primer may be designed to anneal to the exon sequence.

Gene: As used herein a gene is a unit of heredity. Generally, a gene is a portion of DNA that encodes a protein or a functional RNA. A gene is a locatable region of genomic sequence corresponding to a unit of inheritance. A gene may be associated with regulatory regions, transcribed regions, and or other functional sequence regions.

Genotype: As used herein, the term "genotype" refers to the genetic constitution of an organism. More specifically, the term refers to the identity of alleles present in an individual. "Genotyping" of an individual or a DNA sample refers to identifying the nature, in terms of nucleotide base, of the two alleles possessed by an individual at a known polymorphic site.

Gene regulatory element: As used herein a gene regulatory element or regulatory sequence is a segment of DNA where regulatory proteins, such as transcription factors, bind to regulate gene expression. Such regulatory regions are often upstream of the gene being regulated.

Healthy individual: As used herein, the term "healthy individual" or "control" refers to a subject has not been diagnosed with the syndrome and/or disease of interest.

Heterozygous: As used herein, the term "heterozygous" or "HET" refers to an individual possessing two different alleles of the same gene. As used herein, the term "heterozygous" encompasses "compound heterozygous" or "compound heterozygous mutant." As used herein, the term "compound heterozygous" refers to an individual possessing two different alleles. As used herein, the term "compound heterozygous mutant" refers to an individual possessing two different copies of an allele, such alleles are characterized as mutant forms of a gene.

Homozygous: As used herein, the term "homozygous" refers to an individual possessing two copies of the same allele. As used herein, the term "homozygous mutant" refers to an individual possessing two copies of the same allele, such allele being characterized as the mutant form of a gene.

Hybridize: As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

Identity or percent identical: As used herein, the terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In other cases, commercially available software, such as GenomeQuest, may be used to determine percent identity. When utilizing BLAST and Gapped BLAST programs, the default parameters of the respective programs (e.g., BLASTN; available at the Internet site for the National Center for Biotechnology Information) may be used. In one embodiment, the percent identity of two sequences may be determined using GCG with a gap weight of 1, such that each amino acid gap is weighted as if it were a single amino acid mismatch between the two sequences. Or, the ALIGN program (version 2.0), which is part of the GCG (Accelrys, San Diego, Calif.) sequence alignment software package may be used.

As used herein, the term at least 90% identical thereto includes sequences that range from 90 to 100% identity to the indicated sequences and includes all ranges in between. Thus, the term at least 90% identical thereto includes sequences that are 91, 91.5, 92, 92.5, 93, 93.5, 94, 94.5, 95, 95.5, 96, 96.5, 97, 97.5, 98, 98.5, 99, 99.5 percent identical to the indicated sequence. Similarly, the term "at least 70% identical includes sequences that range from 70 to 100% identical, with all ranges in between. The determination of percent identity is determined using the algorithms described herein.

Insertion or addition: As used herein, the term "insertion" or "addition" refers to a change in an amino acid or nucleotide sequence resulting in the addition of one or more amino acid residues or nucleotides, respectively, as compared to the naturally occurring molecule.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Labeled: The terms "labeled" and "labeled with a detectable agent or moiety" are used herein interchangeably to specify that an entity (e.g., a nucleic acid probe, antibody, etc.) can be measured by detection of the label (e.g., visualized, detection of radioactivity and the like) for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

Micro RNA: As used herein microRNAs (miRNAs) are short (20-24 nucleotide) non-coding RNAs that are involved in post-transcriptional regulation of gene expression. microRNA can affect both the stability and translation of mRNAs. For example, microRNAs can bind to complementary sequences in the 3'UTR of target mRNAs and cause gene silencing. miRNAs are transcribed by RNA polymerase II as part of capped and polyadenylated primary transcripts (pri-miRNAs) that can be either protein-coding or non-coding. The primary transcript can be cleaved by the Drosha ribonuclease III enzyme to produce an approximately 70-nucleotide stem-loop precursor miRNA (pre-miRNA), which can further be cleaved by the cytoplasmic Dicer ribonuclease to generate the mature miRNA and antisense miRNA star (miRNA*) products. The mature miRNA can be incorporated into a RNA-induced silencing complex (RISC), which can recognize target mRNAs through imperfect base pairing with the miRNA and most commonly results in translational inhibition or destabilization of the target mRNA.

Multiplex PCR: As used herein, the term "multiplex PCR" refers to concurrent amplification of two or more regions which are each primed using a distinct primers pair.

Multiplex ASPE: As used herein, the term "multiplex ASPE" refers to an assay combining multiplex PCR and allele specific primer extension (ASPE) for detecting polymorphisms. Typically, multiplex PCR is used to first amplify regions of DNA that will serve as target sequences for ASPE primers. See the definition of allele specific primer extension.

Mutation and/or variant: As used herein, the terms mutation and variant are used interchangeably to describe a nucleic acid or protein sequence change. The term "mutant" as used herein refers to a mutated, or potentially non-functional form of a gene. The term includes any mutation that renders a gene not functional from a point mutation to large chromosomal rearrangements as is known in the art.

Nucleic acid: As used herein, a "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

Polypeptide or protein: As used herein, the term "polypeptide" and/or "protein" refers to a polymer of amino acids, and not to a specific length. Thus, peptides, oligopeptides and proteins are included within the definition of polypeptide and/or protein. "Polypeptide" and "protein" are used interchangeably herein to describe protein molecules that may comprise either partial or full-length proteins. The term "peptide" is used to denote a less than full-length protein or a very short protein unless the context indicates otherwise.

As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein. Abbreviations for amino acid residues are the standard 3-letter and/or 1-letter codes used in the art to refer to one of the 20 common L-amino acids.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

Primer: As used herein, the term "primer" refers to a short single-stranded oligonucleotide capable of hybridizing to a complementary sequence in a nucleic acid sample. Typically, a primer serves as an initiation point for template dependent DNA synthesis. Deoxyribonucleotides can be added to a primer by a DNA polymerase. In some embodiments, such deoxyribonucleotides addition to a primer is also known as primer extension. The term primer, as used herein, includes all forms of primers that may be synthesized including peptide nucleic acid primers, locked nucleic acid primers, phosphorothioate modified primers, labeled primers, and the like. A "primer pair" or "primer set" for a PCR reaction typically refers to a set of primers typically including a "forward primer" and a "reverse primer." As used herein, a "forward primer" refers to a primer that anneals to the anti-sense strand of dsDNA. A "reverse primer" anneals to the sense-strand of dsDNA.

Polymorphism: As used herein, the term "polymorphism" refers to the coexistence of more than one form of a gene or portion thereof.

Portion and Fragment: As used herein, the terms "portion" and "fragment" are used interchangeably to refer to parts of a polypeptide, nucleic acid, or other molecular construct.

Sense strand vs. anti-sense strand: As used herein, the term "sense strand" refers to the strand of double-stranded DNA (dsDNA) that includes at least a portion of a coding sequence of a functional protein. As used herein, the term "anti-sense strand" refers to the strand of dsDNA that is the reverse complement of the sense strand.

Significant difference: As used herein, the term "significant difference" is well within the knowledge of a skilled artisan and will be determined empirically with reference to each particular biomarker. For example, a significant difference in the expression of a biomarker in a subject with the disease or syndrome of interest as compared to a healthy subject is any difference in protein amounts which is statistically significant.

Similar or homologue: As used herein, the term "similar" or "homologue" when referring to amino acid or nucleotide sequences means a polypeptide having a degree of homology or identity with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, Proc. Natl. Acad. Sci. USA, 80:726-730). For example, homologous sequences may be taken to include an amino acid sequences which in alternate embodiments are at least 70% identical, 75% identical, 80% identical, 85% identical, 90% identical, 95% identical, 97% identical, or 98% identical to each other.

Specific: As used herein, the term "specific," when used in connection with an oligonucleotide primer, refers to an oligonucleotide or primer, which under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5 M NaHPO$_4$, 7% sodium dodecyl sulfate (SDS), at 65° C., and washing in 0.25 M NaHPO$_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, 4th Ed., Chapter 2, John Wiley & Sons, N.Y). For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [$\gamma$-$^{32}$P]ATP, or incorporation of radiolabeled nucleotides such as [$\alpha$-$^{32}$P]dCTP by random primer labeling. Alternatively, probes may be labeled by incorporation of biotinylated or fluorescein labeled nucleotides, and the probe detected using streptavidin or anti-fluorescein antibodies.

siRNA: As used herein, siRNA (small inhibitory RNA) is essentially a double-stranded RNA molecule composed of about 20 complementary nucleotides. siRNA is created by the breakdown of larger double-stranded (ds) RNA molecules. siRNA can suppress gene expression by inherently splitting its corresponding mRNA in two by way of the interaction of the siRNA with the mRNA, leading to degradation of the mRNA. siRNAs can also interact with DNA to facilitate chromatin silencing and the expansion of heterochromatin.

Subject: As used herein, the term "subject" refers to a human or any non-human animal. A subject can be a patient, which refers to a human presenting to a medical provider for diagnosis or treatment of a disease. A human includes pre and post-natal forms. Also, as used herein, the terms "individual," "subject" or "patient" includes all warm-blooded animals. In one embodiment the subject is a human. In one embodiment, the individual is a subject who has NCGS or has an enhanced risk of developing NCGS.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially complementary: As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

Substitution: As used herein, the term "substitution" refers to the replacement of one or more amino acids or nucleotides by different amino acids or nucleotides, respectively, as compared to the naturally occurring molecule.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Solid support: The term "solid support" or "support" means a structure that provides a substrate onto which biomolecules may be bound. For example, a solid support may be an assay well (i.e., such as a microtiter plate), or the solid support may be a location on an array, or a mobile support, such as a bead.

Upstream and downstream: As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid. Protein, polypeptide and peptide sequences disclosed herein are all listed from N-terminal amino acid to C-terminal acid and nucleic acid sequences disclosed herein are all listed from the 5' end of the molecule to the 3' end of the molecule.

Overview

The disclosure herein provides novel mutations identified in a disease and/or syndrome of interest gene that can be used for more accurate diagnosis of disorders relating to the gene and/or syndrome of interest.

In some embodiments, the sample contains nucleic acid. In some embodiments, the testing step comprises nucleic acid sequencing. In some embodiments, the testing step comprises hybridization. In some embodiments, the hybridization is performed using one or more oligonucleotide probes specific for a region in the biomarker of interest. In some embodiments, for detection of mutations, hybridization is performed under conditions sufficiently stringent to disallow a single nucleotide mismatch. In some embodiments, the hybridization is performed with a microarray. In some embodiments, the testing step comprises restriction enzyme digestion. In some embodiments, the testing step comprises PCR amplification. In some embodiments, the PCR amplification is digital PCR amplification. In some embodiments, the testing step comprises primer extension. In some embodiments, the primer extension is single-base primer extension. In some embodiments, the testing step comprises performing a multiplex allele-specific primer extension (ASPE).

In some embodiments, the sample contains protein. In some embodiments, the testing step comprises amino acid sequencing. In some embodiments, the testing step comprises performing an immunoassay using one or more antibodies that specifically recognize the biomarker of interest. In some embodiments, the testing step comprises protease digestion (e.g., trypsin digestion). In some embodiments, the testing step further comprises performing 2D-gel electrophoresis.

In some embodiments, the testing step comprises determining the presence of the one or more biomarkers using mass spectrometry. In some embodiments, the mass spectrometric format is selected from among Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

In some embodiments, the sample is obtained from cells, tissue, whole blood, mouthwash, plasma, serum, urine, stool, saliva, cord blood, chorionic villus sample, chorionic villus sample culture, amniotic fluid, amniotic fluid culture, transcervical lavage fluid, or combination thereof. In further embodiments, the sample is obtained from blood or blood products (e.g., plasma or serum) from a pregnant woman and/or fetal DNA.

In some embodiments, the testing step comprises determining the identity of the nucleotide and/or amino acid at a pre-determined position in the biomarker. In some embodiments, the presence of the mutation is determined by comparing the identity of the nucleotide and/or amino acid at the pre-determined position to a control.

In embodiments, the method may comprise performing the assay (e.g., sequencing) in a plurality of individuals to determine the statistical significance of the association.

In another aspect, the disclosure provides reagents for detecting the biomarker of interest such as, but not limited to a nucleic acid probe that specifically binds to the biomarker (e.g., a mutation in a DNA sequence), or an array containing one or more probes that specifically bind to the biomarker. In some embodiments, the disclosure provides an antibody that specifically binds to the biomarker. In some embodiments, the disclosure provides a kit for comprising one or more of such reagents. In some embodiments, the one or more reagents are provided in a form of microarray. In some embodiments, the kit further comprises reagents for primer extension. In some embodiments, the kit further comprises a control indicative of a healthy individual. In some embodiments, the kit further comprises an instructions on how to determine if an individual has the syndrome or disease of interest based on the biomarker of interest.

In some cases, the amount of the one or more biomarkers may, in certain embodiments, be detected by: (a) detecting the amount of a polypeptide or protein which is regulated by said one or more biomarker; (b) detecting the amount of a polypeptide or protein which regulates said biomarker; or (c) detecting the amount of a metabolite of the biomarker.

In still another aspect, the disclosure herein provides a computer readable medium encoding information corresponding detection of the biomarker.

Methods and Compositions for Diagnosing NCGS

Embodiments of the present disclosure comprise compositions and methods for diagnosing presence or increased risk of developing non-coeliac gluten sensitivity (NCGS). The methods and compositions of the present disclosure may be used to obtain or provide genetic information from a subject in order to objectively diagnose the presence or increased risk for that subject, or other subjects to develop NCGS. The methods and compositions may be embodied in a variety of ways.

In one embodiment, disclosed is a method to detect a biomarker associated with non-coeliac gluten sensitivity (NCGS) in an individual comprising the steps of: obtaining a sample from the individual; and measuring the amount of at least one of IL-8, IL-10, TNF-Alpha or total IgE protein in the sample. In some cases, the measuring may further comprise measuring expression of one of IP-10, CD4 or CD45. Additionally and/or alternatively, the method may include measurement of at least one normalization (e.g., housekeeping) gene. In one non-limiting embodiment, the housekeeping gene may be glyceraldehyde 3-phosphate dehydrogenase. Or, other house keeping genes may be used. Additionally and/or alternatively, other biomarkers may be measured.

As disclosed herein, a variety of methods may be used to measure the biomarkers of interest. In one embodiment, the measuring comprises measuring peptide or polypeptide biomarkers. For example, in one embodiment, the measuring comprises an immunoassay. Or, the measuring may comprise flow cytometry. Or, as discussed in detail herein, nucleic acid methods may be used.

A variety of sample types may be used. In certain embodiments, the sample comprises blood, serum, plasma, or a tissue biopsy.

In certain embodiments, the disclosure provides a method of identifying a marker associated with NCGS in an individual. The method may comprise the steps of identifying at least one marker having increased or decreased expression in NCGS, but not in coeliac disease as compared to a control individual or population.

In other embodiments, the disclosure provides a method to detect the presence of, or susceptibility to, non-coeliac gluten sensitivity (NCGS) in an individual. The method may comprise the steps of obtaining a sample from the individual; measuring the amount of at least one of IL-8, IL-10, TNF-Alpha or total IgE protein in the sample; and comparing the expression of the at least one of IL-8, IL-10, TNF-alpha or total IgE in the sample with a control value for each of the IL-8, IL-10, TNF-alpha or total IgE. In some cases, the measuring may further comprise measuring expression of at least one of IP-10, CD4 or CD45 and comparing the levels of these markers with that of a control value. In an embodiment, the control value is derived from is a healthy individual or individuals with no detected or detectable gastrointestinal pathology. In some embodiments, the control is a disease control. Such disease controls may include individuals with coeliac disease (stratified by whether the individual is on a gluten-free diet or not on a gluten free diet) and subjects with other GI diseases such as inflammatory bowel disease (IBD), hepatitis, small intestinal bacterial overgrowth, and other diseases.

Additionally and/or alternatively, the method may include measurement of at least one normalization (e.g., housekeeping) gene. In one non-limiting embodiment, the housekeeping gene may be glyceraldehyde 3-phosphate dehydrogenase. Or, other housekeeping genes may be used. Additionally and/or alternatively, other biomarkers may be measured.

As disclosed herein, a variety of methods may be used to measure the biomarkers of interest. In one embodiment, the measuring comprises measuring peptide or polypeptide biomarkers. For example, in one embodiment, the measuring comprises an immunoassay. Or, the measuring may comprise flow cytometry. Or, as discussed in detail herein, nucleic acid methods may be used.

A variety of sample types may be used. In certain embodiments, the sample comprises blood, serum, plasma or a tissue biopsy.

Yet other embodiments comprise a composition to detect biomarkers associated with non-coeliac gluten sensitivity (NCGS) in an individual. In certain embodiments, the composition comprises reagents that quantify the levels of at least one of IL-8, IL-10, TNF-alpha or total IgE protein in a biological sample. In some cases, the composition may further comprise reagents for measuring expression of at least one of IP-10, CD4 or CD45.

For example, as described in detail herein the composition may comprise reagents to measure peptide or polypeptide biomarkers. In one embodiment, the composition comprises reagents to perform an immunoassay. Or, the composition may comprise reagents to perform flow cytometry. Or, as discussed in detail herein, the composition may comprise reagents to determine the presence of a particular sequence and/or expression level of a nucleic acid.

Other embodiments include kits that contain at least some of the compositions disclosed herein and/or reagents for performing the methods disclosed herein. Such kits may include control biological samples from is a healthy individual or individuals with no detected or detectable gastrointestinal pathology. In some embodiments, the control is a disease control. Such disease controls may include individuals with coeliac disease (stratified by whether the individual is on a gluten-free diet or not on a gluten free diet) and subjects with other GI diseases such as inflammatory bowel disease (IBD), hepatitis, small intestinal bacterial overgrowth, and other diseases. Such kits may include instructions and/or computer-readable media comprising instructions and/or other information for performing the methods. Such instructions may comprise control values as described herein.

Other embodiments comprise computer-readable media comprising instructions and/or other information for performing the methods independent of a kit or reagents therein.

Peptide, Polypeptide and Protein Assays

In certain embodiments, the biomarker of interest is detected at the protein (or peptide or polypeptide level), that is, a gene product is analyzed. For example, a protein or fragment thereof can be analyzed by amino acid sequencing methods, or immunoassays using one or more antibodies that specifically recognize one or more epitopes present on the biomarker of interest, or in some cases specific to a mutation of interest. Proteins can also be analyzed by protease digestion (e.g., trypsin digestion) and, in some embodiments, the digested protein products can be further analyzed by 2D-gel electrophoresis.

Antibody Detection

Specific antibodies that bind the biomarker of interest can be employed in any of a variety of methods known in the art. Antibodies against particular epitopes, polypeptides, and/or proteins can be generated using any of a variety of known methods in the art. For example, the epitope, polypeptide, or protein against which an antibody is desired can be produced and injected into an animal, typically a mammal (such as a donkey, mouse, rabbit, horse, chicken, etc.), and antibodies produced by the animal can be collected from the animal. Monoclonal antibodies can also be produced by generating hybridomas that express an antibody of interest with an immortal cell line.

In some embodiments, antibodies are labeled with a detectable moiety as described herein.

Antibody detection methods are well known in the art including, but are not limited to, enzyme-linked immunoadsorbent assays (ELISAs) and Western blots. Some such methods are amenable to being performed in an array format.

For example, in some embodiments, the biomarker of interest is detected using a first antibody (or antibody fragment) that specifically recognizes the biomarker. The antibody may be labeled with a detectable moiety (e.g., a chemiluminescent molecule), an enzyme, or a second binding agent (e.g., streptavidin). Or, the first antibody may be detected using a second antibody, as is known in the art.

In certain embodiments, the method may further comprise adding a capture support, the capture support comprising at least one capture support binding agent that recognizes and binds to the biomarker so as to immobilize the biomarker on the capture support. The method may, in certain embodiments, further comprise adding a second binding agent that can specifically recognize and bind to at least some of the plurality binding agent molecules on the capture support. In an embodiment, the binding agent that can specifically recognize and bind to at least some of the plurality binding agent molecules on the capture support is a soluble binding agent (e.g., a secondary antibody). The second binding agent may be labeled (e.g., with an enzyme) such that binding of the biomarker of interest is measured by adding a substrate for the enzyme and quantifying the amount of product formed.

In an embodiment, the capture solid support may be an assay well (i.e., such as a microtiter plate). Or, the capture solid support may be a location on an array, or a mobile support, such as a bead. Or the capture support may be a filter.

In some cases, the biomarker may be allowed to complex with a first binding agent (e.g., primary antibody specific for the biomarker and labeled with detectable moiety) and a second binding agent (e.g., a secondary antibody that recognizes the primary antibody or a second primary antibody), where the second binding agent is complexed to a third binding agent (e.g., biotin) that can then interact with a capture support (e.g., magnetic bead) having a reagent (e.g., streptavidin) that recognizes the third binding agent linked to the capture support. The complex (labeled primary antibody: biomarker: second primary antibody-biotin: streptavidin-bead may then be captured using a magnet (e.g., a magnetic probe) to measure the amount of the complex.

A variety of binding agents may be used in the methods of the disclosure. For example, the binding agent attached to the capture support, or the second antibody, may be either an antibody or an antibody fragment that recognizes the biomarker. Or, the binding agent may comprise a protein that binds a non-protein target (i.e., such as a protein that specifically binds to a small molecule biomarker, or a receptor that binds to a protein).

In certain embodiments, the solid supports may be treated with a passivating agent. For example, in certain embodiments the biomarker of interest may be captured on a passivated surface (i.e., a surface that has been treated to reduce non-specific binding). One such passivating agent is BSA. Additionally and/or alternatively, where the binding agent used is an antibody, the solid supports may be coated with protein A, protein G, protein A/G, protein L, or another agent that binds with high affinity to the binding agent (e.g., antibody). These proteins bind the Fc domain of antibodies and thus can orient the binding of antibodies that recognize the protein or proteins of interest.

Nucleic Acid Assays

In certain embodiments, the biomarkers disclosed herein are detected at the nucleic acid level. In one embodiment, the disclosure comprises methods for diagnosing the presence or an increased risk of developing the syndrome or disease of interest (e.g., NCGS) in a subject. The method may comprise the steps of obtaining a nucleic acid from a tissue or body fluid sample from a subject and conducting an assay to identify whether there is a variant sequence (i.e., a mutation) in the subject's nucleic acid. In certain embodiments, the method may comprise comparing the variant to known variants associated with the syndrome or disease of interest and determining whether the variant is a variant that has been previously identified as being associated with the syndrome or disease of interest. Or, the method may comprise identifying the variant as a new, previously uncharacterized variant. If the variant is a new variant, the method may further comprise performing an analysis to determine whether the mutation is expected to be deleterious to expression of the gene and/or the function of the protein encoded by the gene. The method may further comprise using the variant profile (i.e., the compilation of mutations identified in the subject) to diagnose the presence of the syndrome or disease of interest or an increased risk of developing the syndrome or disease of interest.

Nucleic acid analyses can be performed on genomic DNA, messenger RNAs, and/or cDNA. Also, in various embodiments, the nucleic acid comprises a gene, an RNA, an exon, an intron, a gene regulatory element, an expressed RNA, an siRNA, or an epigenetic element. Also, regulatory elements, including splice sites, transcription factor binding, A-I editing sites, microRNA binding sites, and functional RNA structure sites may be evaluated for mutations (i.e., variants). Thus, for each of the methods and compositions of the disclosure, the variant may comprise a nucleic acid sequence that encompasses at least one of the following: (1) A-to-I editing sites; (2) splice sites; (3) conserved functional RNA structures; (4) validated transcription factor binding sites (TFBS); (5) microRNA (miRNA) binding sites; (6) polyadenylation sites; (7) known regulatory elements; (8) miRNA genes; (9) small nucleolar RNA genes encoded in the ROIs; and/or (10) ultraconserved elements across placental mammals.

In many embodiments, nucleic acids are extracted from a biological sample. In some embodiments, the nucleic acid is cell-free DNA. In some embodiments, nucleic acids are analyzed without having been amplified. In some embodiments, nucleic acids are amplified using techniques known in the art (such as polymerase chain reaction (PCR)) and amplified nucleic acids are used in subsequent analyses. Multiplex PCR, in which several amplicons (e.g., from different genomic regions) are amplified at once using multiple sets of primer pairs, may be employed. For example, nucleic acid can be analyzed by sequencing, hybridization, PCR amplification, restriction enzyme digestion, primer extension such as single-base primer extension or multiplex allele-specific primer extension (ASPE), or DNA sequencing. In some embodiments, nucleic acids are amplified in a manner such that the amplification product for a wild-type allele differs in size from that of a mutant allele. Thus, presence or absence of a particular mutant allele can be determined by detecting size differences in the amplification products, e.g., on an electrophoretic gel. For example, deletions or insertions of gene regions may be particularly amenable to using size-based approaches.

Certain exemplary nucleic acid analysis methods are described in detail below.

Allele-Specific Amplification

In some embodiments, for example, where the biomarker for the disease and/or syndrome of interest is a mutation, a biomarker is detected using an allele-specific amplification assay. This approach is variously referred to as PCR amplification of specific allele (PASA) (Sarkar, et al., 1990 *Anal. Biochem.* 186:64-68), allele-specific amplification (ASA) (Okayama, et al., 1989 *J. Lab. Clin. Med.* 114:105-113), allele-specific PCR (ASPCR) (Wu, et al. 1989 *Proc. Natl. Acad. Sci. USA.* 86:2757-2760), and amplification-refractory mutation system (ARMS) (Newton, et al., 1989 *Nucleic Acids Res.* 17:2503-2516). The entire contents of each of these references is incorporated herein. This method is applicable for single base substitutions as well as micro deletions/insertions.

For example, for PCR-based amplification methods, amplification primers may be designed such that they can distinguish between different alleles (e.g., between a wild-type allele and a mutant allele). Thus, the presence or absence of amplification product can be used to determine whether a gene mutation is present in a given nucleic acid sample. In some embodiments, allele specific primers can be designed such that the presence of amplification product is indicative of the gene mutation. In some embodiments, allele specific primers can be designed such that the absence of amplification product is indicative of the gene mutation.

In some embodiments, two complementary reactions are used. One reaction employs a primer specific for the wild type allele ("wild-type-specific reaction") and the other reaction employs a primer for the mutant allele ("mutant-specific reaction"). The two reactions may employ a common second primer. PCR primers specific for a particular allele (e.g., the wild-type allele or mutant allele) generally perfectly match one allelic variant of the target, but are mismatched to other allelic variant (e.g., the mutant allele or wild-type allele). The mismatch may be located at/near the 3' end of the primer, leading to preferential amplification of the perfectly matched allele. Whether an amplification product can be detected from one or in both reactions indicates the absence or presence of the mutant allele. Detection of an amplification product only from the wild-type-specific reaction indicates presence of the wild-type allele only (e.g., homozygosity of the wild-type allele). Detection of an amplification product in the mutant-specific reaction only indicates presence of the mutant allele only (e.g. homozygosity of the mutant allele). Detection of amplification products from both reactions indicate (e.g., a heterozygote). As used herein, this approach will be referred to as "allele specific amplification (ASA)."

Allele-specific amplification can also be used to detect duplications, insertions, or inversions by using a primer that hybridizes partially across the junction. The extent of junction overlap can be varied to allow specific amplification.

Amplification products can be examined by methods known in the art, including by visualizing (e.g., with one or more dyes) bands of nucleic acids that have been migrated (e.g., by electrophoresis) through a gel to separate nucleic acids by size.

Allele-Specific Primer Extension

In some embodiments, an allele-specific primer extension (ASPE) approach is used to detect a gene mutations. ASPE employs allele-specific primers that can distinguish between alleles (e.g., between a mutant allele and a wild-type allele) in an extension reaction such that an extension product is obtained only in the presence of a particular allele (e.g., mutant allele or wild-type allele). Extension products may be detectable or made detectable, e.g., by employing a labeled deoxynucleotide in the extension reaction. Any of a variety of labels are compatible for use in these methods, including, but not limited to, radioactive labels, fluorescent labels, chemiluminescent labels, enzymatic labels, etc. In some embodiments, a nucleotide is labeled with an entity that can then be bound (directly or indirectly) by a detectable label, e.g., a biotin molecule that can be bound by streptavidin-conjugated fluorescent dyes. In some embodiments, reactions are done in multiplex, e.g., using many allele-specific primers in the same extension reaction.

In some embodiments, extension products are hybridized to a solid or semi-solid support, such as beads, matrix, gel, among others. For example, the extension products may be tagged with a particular nucleic acid sequence (e.g., included as part of the allele-specific primer) and the solid support may be attached to an "anti-tag" (e.g., a nucleic acid sequence complementary to the tag in the extension product). Extension products can be captured and detected on the solid support. For example, beads may be sorted and detected. One such system that can be employed in this manner is the LUMINEX™ MAP system, which can be adapted for cystic fibrosis mutation detection by Bioscience™ and is sold commercially as a universal bead array (TAG-IT™)

Single Nucleotide Primer Extension

In some embodiments, a single nucleotide primer extension (SNuPE) assay is used, in which the primer is designed to be extended by only one nucleotide. In such methods, the identity of the nucleotide just downstream of the 3' end of the primer is known and differs in the mutant allele as compared to the wild-type allele. SNuPE can be performed using an extension reaction in which the only one particular kind of deoxynucleotide is labeled (e.g., labeled dATP, labeled dCTP, labeled dGTP, or labeled dTTP). Thus, the presence of a detectable extension product can be used as an indication of the identity of the nucleotide at the position of interest (e.g., the position just downstream of the 3' end of the primer), and thus as an indication of the presence or absence of a mutation at that position. SNuPE can be performed as described in U.S. Pat. Nos. 5,888,819; 5,846,710; 6,280,947; 6,482,595; 6,503,718; 6,919,174; Piggee, C. et al. *Journal of Chromatography* A 781 (1997), p. 367-375 ("Capillary Electrophoresis for the Detection of Known Point Mutations by Single-Nucleotide Primer Extension and Laser-Induced Fluorescence Detection"); Hoogendoom, B. et al., *Human Genetics* (1999) 104:89-93, ("Genotyping Single Nucleotide Polymorphism by Primer Extension and High Performance Liquid Chromatography"), the entire contents of each of which are herein incorporated by reference.

In some embodiments, primer extension can be combined with mass spectrometry for accurate and fast detection of the presence or absence of a mutation. See, U.S. Pat. No. 5,885,775 to Haff et al. (analysis of single nucleotide polymorphism analysis by mass spectrometry); U.S. Pat. No. 7,501,251 to Koster (DNA diagnosis based on mass spectrometry); the teachings of both of which are incorporated herein by reference. Suitable mass spectrometric format includes, but is not limited to, Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

Oligonucleotide Ligation Assay

In some embodiments, an oligonucleotide ligation assay ("OLA" or "OL") is used. OLA employs two oligonucleotides that are designed to be capable of hybridizing to abutting sequences of a single strand of a target molecules. Typically, one of the oligonucleotides is biotinylated, and the other is detectably labeled, e.g., with a streptavidin-conjugated fluorescent moiety. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241: 1077-1080 and U.S. Pat. No. 4,998,617, the entire contents of which are herein incorporated by reference in their entirety.

Hybridization Approach

In some embodiments, nucleic acids are analyzed by hybridization using one or more oligonucleotide probes specific for the biomarker of interest and under conditions sufficiently stringent to disallow a single nucleotide mismatch. In certain embodiments, suitable nucleic acid probes can distinguish between a normal gene and a mutant gene. Thus, for example, one of ordinary skill in the art could use probes of the invention to determine whether an individual is homozygous or heterozygous for a particular allele.

Nucleic acid hybridization techniques are well known in the art. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

In some embodiments, probe molecules that hybridize to the mutant or wildtype sequences can be used for detecting such sequences in the amplified product by solution phase or, more preferably, solid phase hybridization. Solid phase hybridization can be achieved, for example, by attaching probes to a microchip.

Nucleic acid probes may comprise ribonucleic acids and/or deoxyribonucleic acids. In some embodiments, provided nucleic acid probes are oligonucleotides (i.e., "oligonucleotide probes"). Generally, oligonucleotide probes are long enough to bind specifically to a homologous region of the gene of interest, but short enough such that a difference of one nucleotide between the probe and the nucleic acid sample being tested disrupts hybridization. Typically, the sizes of oligonucleotide probes vary from approximately 10 to 100 nucleotides. In some embodiments, oligonucleotide probes vary from 15 to 90, 15 to 80, 15 to 70, 15 to 60, 15 to 50, 15 to 40, 15 to 35, 15 to 30, 18 to 30, or 18 to 26 nucleotides in length. As appreciated by those of ordinary skill in the art, the optimal length of an oligonucleotide probe may depend on the particular methods and/or conditions in which the oligonucleotide probe may be employed.

In some embodiments, nucleic acid probes are useful as primers, e.g., for nucleic acid amplification and/or extension reactions. For example, in certain embodiments, the gene sequence being evaluated for a variant comprises the exon sequences. In certain embodiments, the exon sequence and additional flanking sequence (e.g., about 5, 10, 15, 20, 25, 30, 35, 40, 45, 50, 55 or more nucleotides of UTR and/or intron sequence) is analyzed in the assay. Or, intron sequences or other non-coding regions may be evaluated for potentially deleterious mutations. Or, portions of these sequences may be used. Such variant gene sequences may include sequences having at least one of the mutations as described herein.

Other embodiments of the disclosure provide isolated gene sequences containing mutations that relate to the syndrome and/or disease of interest. Such gene sequences may be used to objectively diagnose the presence or increased risk for a subject to develop NCGS. In certain embodiments, the isolated nucleic acid may contain a non-variant sequence or a variant sequence of any one or combination thereof. For example, in certain embodiments, the gene sequence comprises the exon sequences. In certain embodiments, the exon sequence and additional flanking sequence (e.g., about 5, 10, 15, 20, 25, 30, 35, 40, 45, 50, 55 or more nucleotides of UTR and/or intron sequence) is analyzed in the assay. Or, intron sequences or other non-coding regions may be used. Or, portions of these sequences may be used. In certain embodiments, the gene sequence comprises an exon sequence from at least one of the biomarker genes disclosed herein.

In some embodiments, nucleic acid probes are labeled with a detectable moiety as described herein.

Arrays

A variety of the methods mentioned herein may be adapted for use with arrays that allow sets of biomarkers to be analyzed and/or detected in a single experiment. For example, multiple mutations that comprise biomarkers can be analyzed at the same time. In particular, methods that involve use of nucleic acid reagents (e.g., probes, primers, oligonucleotides, etc.) are particularly amenable for adaptation to an array-based platform (e.g., microarray). In some embodiments, an array containing one or more probes specific for detecting mutations in the biomarker of interest.

DNA Sequencing

In certain embodiments, diagnosis of the biomarker of interest is carried out by detecting variation in the sequence, genomic location or arrangement, and/or genomic copy number of a nucleic acid or a panel of nucleic acids by nucleic acid sequencing.

In some embodiments, the method may comprise obtaining a nucleic acid from a tissue or body fluid sample from a subject and sequencing at least a portion of a nucleic acid in order to obtain a sample nucleic acid sequence for at least one gene. In certain embodiments, the method may comprise comparing the variant to known variants associated with NCGS and determining whether the variant is a variant that has been previously identified as being associated with NCGS. Or, the method may comprise identifying the variant as a new, previously uncharacterized variant. If the variant is a new variant, or in some cases for previously characterized (i.e., identified) variants, the method may further comprise performing an analysis to determine whether the mutation is expected to be deleterious to expression of the gene and/or the function of the protein encoded by the gene. The method may further comprise using the variant profile (i.e., a compilation of variants identified in the subject) to diagnose the presence of NCGS or an increased risk of developing NCGS.

For example, in certain embodiments, next generation (massively-parallel sequencing) may be used. Or, Sanger sequencing may be used. Or, a combination of next-generation (massively-parallel sequencing) and Sanger sequencing may be used. Additionally and/or alternatively, the sequencing comprises at least one of single-molecule sequencing-by-synthesis. Thus, in certain embodiments, a plurality of DNA samples are analyzed in a pool to identify samples that show a variation. Additionally or alternatively, in certain embodiments, a plurality of DNA samples are analyzed in a plurality of pools to identify an individual sample that shows the same variation in at least two pools.

One conventional method to perform sequencing is by chain termination and gel separation, as described by Sanger et al., 1977, Proc Natl Acad Sci USA, 74:5463-67. Another conventional sequencing method involves chemical degradation of nucleic acid fragments. See, Maxam et al., 1977, Proc. Natl. Acad. Sci., 74:560-564. Also, methods have been developed based upon sequencing by hybridization. See, e.g., Harris et al., U.S. Patent Application Publication No. 20090156412. Each of these references are incorporated by reference in there entireties herein.

In other embodiments, sequencing of the nucleic acid is accomplished by massively parallel sequencing (also known as "next generation sequencing") of single-molecules or groups of largely identical molecules derived from single molecules by amplification through a method such as PCR. Massively parallel sequencing is shown for example in Lapidus et al., U.S. Pat. No. 7,169,560, Quake et al. U.S. Pat. No. 6,818,395, Harris U.S. Pat. No. 7,282,337 and Braslavsky, et al., PNAS (USA), 100: 3960-3964 (2003), the contents of each of which are incorporated by reference herein.

In next generation sequencing, PCR or whole genome amplification can be performed on the nucleic acid in order to obtain a sufficient amount of nucleic acid for analysis. In some forms of next generation sequencing, no amplification is required because the method is capable of evaluating DNA sequences from unamplified DNA. Once determined, the sequence and/or genomic arrangement and/or genomic copy number of the nucleic acid from the test sample is compared to a standard reference derived from one or more individuals not known to suffer from NCGS at the time their sample was taken. All differences between the sequence and/or genomic arrangement and/or genomic arrangement and/or copy number of the nucleic acid from the test sample and the standard reference are considered variants.

In next generation (massively parallel sequencing), all regions of interest are sequenced together, and the origin of each sequence read is determined by comparison (alignment) to a reference sequence. The regions of interest can be enriched together in one reaction, or they can be enriched separately and then combined before sequencing. In certain embodiments, and as described in more detail in the examples herein, the DNA sequences derived from coding exons of genes included in the assay are enriched by bulk hybridization of randomly fragmented genomic DNA to specific RNA probes. The same adapter sequences are attached to the ends of all fragments, allowing enrichment of all hybridization-captured fragments by PCR with one primer pair in one reaction. Regions that are less efficiently captured by hybridization are amplified by PCR with specific primers. In addition, PCR with specific primers is may be used to amplify exons for which similar sequences ("pseudo exons") exist elsewhere in the genome.

In certain embodiments where massively parallel sequencing is used, PCR products are concatenated to form long stretches of DNA, which are sheared into short fragments (e.g., by acoustic energy). This step ensures that the fragment ends are distributed throughout the regions of interest. Subsequently, a stretch of dA nucleotides is added to the 3' end of each fragment, which allows the fragments to bind to a planar surface coated with oligo(dT) primers (the "flow cell"). Each fragment may then be sequenced by extending the oligo(dT) primer with fluorescently-labeled nucleotides. During each sequencing cycle, only one type of nucleotide (A, G, T, or C) is added, and only one nucleotide is allowed to be incorporated through use of chain terminating nucleotides. For example, during the 1st sequencing cycle, a fluorescently labeled dCTP could be added. This nucleotide will only be incorporated into those growing complementary DNA strands that need a C as the next nucleotide. After each sequencing cycle, an image of the flow cell is taken to determine which fragment was extended. DNA strands that have incorporated a C will emit light, while DNA strands that have not incorporated a C will appear dark. Chain termination is reversed to make the growing DNA strands extendible again, and the process is repeated for a total of 120 cycles.

The images are converted into strings of bases, commonly referred to as "reads," which recapitulate the 3' terminal 25 to 60 bases of each fragment. The reads are then compared to the reference sequence for the DNA that was analyzed. Since any given string of 25 bases typically only occurs once in the human genome, most reads can be "aligned" to one specific place in the human genome. Finally, a consensus sequence of each genomic region may be built from the available reads and compared to the exact sequence of the reference at that position. Any differences between the consensus sequence and the reference are called as sequence variants.

Detectable Moieties

In certain embodiments, certain molecules (e.g., nucleic acid probes, antibodies, etc.) used in accordance with and/or provided by the invention comprise one or more detectable entities or moieties, i.e., such molecules are "labeled" with such entities or moieties.

Any of a wide variety of detectable agents can be used in the practice of the disclosure. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of some detectable moieties that may be used.

Fluorescent Dyes

In certain embodiments, a detectable moiety is a fluorescent dye. Numerous known fluorescent dyes of a wide variety of chemical structures and physical characteristics are suitable for use in the practice of the disclosure. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Q-DOTS. Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92:4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described, for example, in U.S. Pat. No. 5,945,526 to Lee et al., the entire contents of which are herein incorporated by reference. Donor/acceptor pairs of dyes that can be used include, for example, fluorescein/tetramethylrohdamine, IAEDANS/fluroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

Enzymes

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., 3H, 13C, 14C, 18F, 19F, 32P, 35S, 64Cu, 67Cu, 67Ga, 90Y, 99mTc, 111In, 125I, 123I, 129I, 131I, 135I, 186Re, 187Re, 201Tl, 212Bi, 213Bi, 211At, 153Sm, 177Lu).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Kits

In certain embodiments, the disclosure provides kits for use in accordance with methods and compositions disclosed herein. Generally, kits comprise one or more reagents detect the biomarker of interest. Suitable reagents may include nucleic acid probes and/or antibodies or fragments thereof. In some embodiments, suitable reagents are provided in a form of an array such as a microarray or a mutation panel.

In some embodiments, provided kits further comprise reagents for carried out various detection methods described herein (e.g., sequencing, hybridization, primer extension, multiplex ASPE, immunoassays, etc.). For example, kits may optionally contain buffers, enzymes, and/or reagents for use in methods described herein, e.g., for amplifying nucleic acids via primer-directed amplification, for performing ELISA experiments, etc.

In some embodiments, provided kits further comprise a control indicative of a healthy individual, e.g., a nucleic acid and/or protein sample from an individual who does not have the disease and/or syndrome of interest. In an embodiment, the control is derived from is a healthy individual or individuals with no detected or detectable gastrointestinal pathology. In some embodiments, the control is a disease control. Such disease controls may include individuals with coeliac disease (stratified by whether the individual is on a gluten-free diet or not on a gluten free diet) and subjects with other GI diseases such as inflammatory bowel disease (IBD), hepatitis, small intestinal bacterial overgrowth, and other diseases.

Kits may also contain instructions on how to determine if an individual has the disease and/or syndrome of interest, or is at risk of developing the disease and/or syndrome of interest.

In some embodiments, provided is a computer readable medium encoding information corresponding to the biomarker of interest. Such computer readable medium may be included in a kit of the invention.

Methods to Identify NCGS Markers

Data Mining

In certain embodiments of the disclosure, biomarkers are identified using a data mining approach. For example, in some cases public databases (e.g., PubMed) may be searched for genes that have been shown to be linked to (directly or indirectly) to a certain disease. Such genes may then be evaluated as biomarkers. In one embodiment, the results of such an analysis identify IP-10, IL-8, IgE, TNF-alpha, IL-10, CD4 and CD45 as potential markers of interest. FIG. 1 shows an example of a multi-node interaction network identifying markers associated with NCGS, as described in detail in U.S. Provisional Patent Application No. 62/505,536, filed May 12, 2017 and U.S. Provisional Patent Application 62/523,382, filed Jun. 22, 2017, and incorporated by reference in their entireties herein. In the FIGURE, the circled markers comprise the more relevant disease markers.

Molecular

In certain embodiments, the disclosure comprises methods to identify biomarkers for a syndrome or disease of interest (i.e., variants in nucleic acid sequence that are associated with NCGS in a statistically significant manner). The genes and/or genomic regions assayed for new markers may be selected based upon their importance in biochemical pathways that show genetic linkage and/or biological causation to the syndrome and/or disease of interest. Or, the genes and/or genomic regions assayed for markers may be selected based on genetic linkage to DNA regions that are genetically linked to the inheritance of NCGS in families. Or, the genes and/or genomic regions assayed for markers may be evaluated systematically to cover certain regions of chromosomes not yet evaluated.

In other embodiments, the genes or genomic regions evaluated for new markers may be part of a biochemical pathway that may be linked to the development of the syndrome and/or disease of interest (e.g., NCGS). The variants and/or variant combinations may be assessed for their clinical significance based on one or more of the following methods. If a variant or a variant combination is reported or known to occur more often in nucleic acid from subjects with, than in subjects without, the syndrome and/or disease of interest it is considered to be at least potentially predisposing to the syndrome and/or disease of interest. If a variant or a variant combination is reported or known to be transmitted exclusively or preferentially to individuals having the syndrome and/or disease of interest, it is considered to be at least potentially predisposing to the syndrome and/or disease of interest. Conversely, if a variant is found in both populations at a similar frequency, it is less likely to be associated with the development of the syndrome and/or disease of interest.

If a variant or a variant combination is reported or known to have an overall deleterious effect on the function of a protein or a biological system in an experimental model system appropriate for measuring the function of this protein or this biological system, and if this variant or variant combination affects a gene or genes known to be associated with the syndrome and/or disease of interest, it is considered to be at least potentially predisposing to the syndrome and/or disease of interest. For example, if a variant or a variant combination is predicted to have an overall deleterious effect on a protein or gene expression (i.e., resulting in a nonsense mutation, a frameshift mutation, or a splice site mutation, or even a missense mutation), based on the predicted effect on the sequence and/or the structure of a protein or a nucleic acid, and if this variant or variant combination affects a gene or genes known to be associated with the syndrome and/or disease of interest, it is considered to be at least potentially predisposing to the syndrome and/or disease of interest.

Also, in certain embodiments, the overall number of variants may be important. If, in the test sample, a variant or several variants are detected that are, individually or in combination, assessed as at least probably associated with the syndrome and/or disease of interest, then the individual in whose genetic material this variant or these variants were detected can be diagnosed as being affected with or at high risk of developing the syndrome and/or disease of interest.

For example, the disclosure herein provides methods for diagnosing the presence or an increased risk of developing NCGS in a subject. Such methods may include obtaining a nucleic acid from a sample of tissue or body fluid. The method may further include sequencing the nucleic acid or determining the genomic arrangement or copy number of the nucleic acid to detect whether there is a variant or variants in the nucleic acid sequence or genomic arrangement or copy number. The method may further include the steps of assessing the clinical significance of a variant or variants. Such analysis may include an evaluation of the extent of association of the variant sequence in affected populations (i.e., subjects having the disease). Such analysis may also include an analysis of the extent of the effect the mutation may have on gene expression and/or protein function. The method may also include diagnosis the presence or an increased risk of developing NCGS based on the assessment.

The following examples serve to illustrate certain aspects of the disclosure. These examples are in no way intended to be limiting.

Examples

Tumor Necrosis Factor Alpha (TNF-α)

Tumor Necrosis Factor alpha (TNF-α), also known as cachectin and TNFSF1A, is the prototypic ligand of the TNF superfamily. TNF-α plays a central role in inflammation, immune system development, apoptosis, and lipid metabolism. TNF-α is also involved in a number of pathological conditions including asthma, Crohn's disease, rheumatoid arthritis, neuropathic pain, obesity, type 2 diabetes, septic shock, autoimmunity, and cancer.

TNF-α may be measured using the Quantikine assay. The Quantikine TNF-α immunoassay is a 4.0 hour solid phase ELISA designed to measure human TNF-α in serum and plasma. The assay contains *E. coli*-derived recombinant human TNF-α and antibodies raised against the recombinant factor, and employs the quantitative sandwich enzyme immunoassay technique. A monoclonal antibody specific for human TNF-α is pre-coated onto a microplate. Standards and samples are pipetted into the wells and TNF-α present is bound by the immobilized antibody. After washing away any unbound substances, a biotinylated polyclonal antibody specific for human TNF-α is added to the wells, the wells are washed to remove unbound antibody-biotin reagent, and an enzyme-linked streptavidin is added to the wells. After washing, a substrate solution (hydrogen peroxide and tetramethylbenzidine) is added to the wells and color develops in proportion to the amount of TNF-α bound in the initial step. The color development is stopped and the intensity of the color is measured at 450 nm, subtracting readings at 540 nm and 570 nm.

The samples may be serum or plasma. For serum, a serum separator tube (SST) is used and samples are allowed to clot for 30 minutes at room temperature before centrifugation for 15 minutes at 1000×g. The serum is removed and assayed. Samples are used immediately or aliquoted and stored at ≤−20° C. Plasma is collected using EDTA or heparin as an anticoagulant. The samples are centrifuged for 15 minutes at 1000×g within 30 minutes of collection, and samples assayed immediately or aliquoted and stored at ≤−20° C. For both serum and plasma samples, repeated freeze-thaw cycles should be avoided. Generally, grossly hemolyzed samples, high albumin samples, and citrate plasma should not be used.

Interleukin 10 (IL-10)

Interleukin 10 (IL-10), initially designated cytokine synthesis inhibitory factor (CSIF). IL-10 is a pleiotropic cytokine that can exert either immunosuppressive or immunostimulatory effects on a variety of cell types. IL-10 is a potent modulator of monocyte/macrophage function. As a down-regulator of the cell-mediated immune response, IL-10 can suppress the production of prostaglandin E2 and numerous proinflammatory cytokines, including TNF-alpha, IL-1, IL-6, and IL-8 by monocytes following activation. IL-10 also enhances the release of soluble TNF receptors and inhibits the expression of surface ICAM-1 and B. IL-10 has been reported to suppress the synthesis of superoxide anion phis reactive oxygen intermediates (ROI), and either inhibit or facilitate NO synthesis, depending on the time of exposure to activated macrophages. IL-10 also has marked effects on B cells. For example, it induces IgA synthesis in CD40-activated cells and selects for the secretion of IgG1 and IgG3. IL-10 also has documented activity on endothelial cells, where it mimics IL-4, and on thymocytes and mast cells, where it acts as a growth co-stimulator.

IL-10 may be measured using the Quantikine assay. The Quantikine IL-10 Immunoassay is a 3.5-4.5 hour solid phase ELISA designed to measure IL-10 in cell culture supernatants, serum, and plasma. It contains Sf 21-expressed recombinant human IL-10 and antibodies raised against the recombinant factor. The assay employs a quantitative sandwich enzyme immunoassay technique. A monoclonal antibody specific for IL-10 is pre-coated onto a microplate. Standards and samples are pipetted into the wells and any IL-10 present is bound by the immobilized antibody. After washing away any unbound substances, an enzyme-linked monoclonal antibody specific for IL-10 is added to the wells. After washing, a substrate solution (hydrogen peroxide and tetramethylbenzidine) is added to the wells and color develops in proportion to the amount of TNF-α bound in the initial step. The color development is stopped and the intensity of the color is measured at 450 nm, subtracting readings at 540 nm and 570 nm.

For cell culture supernatants, particulates are removed by centrifugation. Samples are assayed immediately or aliquoted and stored at ≤−20° C. Repeated freeze-thaw cycles should be avoided. For serum, a serum separator tube (SST) is used and samples are allowed to clot for 30 minutes at room temperature before centrifugation for 15 minutes at 1000×g. The serum is removed and assayed. Samples are used immediately or aliquoted and stored at ≤−20° C. Plasma is collected using EDTA or heparin as an anticoagulant. The samples are centrifuged for 15 minutes at 1000×g within 30 minutes of collection, and samples assayed immediately or aliquoted and stored samples at ≤−20° C. For both serum and plasma samples, repeated freeze-thaw cycles should be avoided. Generally, grossly hemolyzed samples and high albumin samples should not be used.

Interleukin 8 (IL-8)

Interleukin 8 (IL-8), a member of the neutrophil-specific CXC subfamily of chemokines, is a potent neutrophil chemotactic and activating factor. It is a primary inflammatory cytokine produced by many cells (including monocytes/macrophages, T cells, neutrophils, fibroblasts, endothelial cells, keratinocytes, hepatocytes, astrocytes and chondrocytes) in response to proinflammatory stimuli such as IL-1, TNF, LPS and viruses. Its function is, in part, to attract neutrophils to the site of inflammation and to activate them. IL-8 binds to two seven-transmembrane, G protein-coupled receptors, CXCR1 and CXCR2, as well as to the non-signalling Duffy antigen on red blood cells. The Duffy antigen may play a role in regulating IL-8 activity on functional receptors.

IL-8 can be measured using the Quantikine assay. The Quantikine IL-8 immunoassay is a 3.5 hour solid phase ELISA designed to measure human IL-8 in cell culture supernatants, serum, and plasma. It is based on antibodies raised against the 72 amino acid variant of human IL-8 derived from *E. coli*. It is calibrated with the same recombinant factor. The assay employs the quantitative sandwich enzyme immunoassay, technique. A monoclonal antibody specific for IL-8 has been pre-coated onto a microplate. Standards and samples are pipetted into the wells and any IL-8 present is bound by the immobilized antibody. After washing away any unbound substances, an enzyme-linked monoclonal antibody specific for IL-8 is added to the wells. After washing, a substrate solution (hydrogen peroxide and tetramethylbenzidine) is added to the wells and color develops in proportion to the amount of TNF-α bound in the initial step. The color development is stopped and the intensity of the color is measured at 450 nm, subtracting readings at 540 nm and 570 nm.

For cell culture supernatants, particulates are removed by centrifugation. Samples are assayed immediately or aliquoted and stored at ≤−20° C. Repeated freeze-thaw cycles should be avoided. For serum, a serum separator tube (SST) is used and samples are allowed to clot for 30 minutes at room temperature before centrifugation for 15 minutes at 1000×g. The serum is removed and assayed. Samples are used immediately or aliquoted and stored at ≤−20° C. Plasma is collected using EDTA or heparin as an anticoagulant. The samples are centrifuged for 15 minutes at 1000×g within 30 minutes of collection, and samples assayed immediately or aliquoted and stored at ≤−20° C. For both serum and plasma samples, repeated freeze-thaw cycles should be avoided. Generally, grossly hemolyzed samples and high albumin samples should not be used.

Total IgE

Immunoglobulin E (IgE) plays an important role in immunological protection against parasitic infections and in allergy (type 1 hypersensitivity). For example, the binding of the allergen to sensitized mast cells or basophilic cells can result in cross-linking of IgE on the cell membrane, leading to cell degranulation and the release of factors (e.g. histamine), which produce the typical symptoms of type 1 hypersensitivity. The IgE concentration in serum is normally very low (<0.001% of the total serum immunoglobulin). The IgE concentration is generally age-dependent, with the lowest values being measured at birth. Its concentration gradually increases and becomes stabilized between the age of 5-7, although the IgE values can vary greatly within particular age groups. In infants and small children with recurrent respiratory tract diseases, the determination of IgE can be of prognostic relevance. As IgE is of importance in allergies, elevated IgE concentrations can be found in patients with allergic diseases such as hay fever, atopic bronchitis and dermatitis. Elevated serum IgE concentrations can also occur in non-allergic diseases, e.g. bronchopulmonary aspergillosis, Wiskott-Aldrich syndrome, hyper-IgE syndrome, IgE myeloma, and parasitic infections.

The IgE II assay (Elecsys) uses monoclonal antibodies specifically directed against human IgE. The Elecsys assay is a sandwich immunoassay. During the first incubation, IgE in the sample (10 μL) is mixed with a biotinylated monoclonal IgE-specific antibody, and a monoclonal IgE-specific antibody labeled with a ruthenium complex (Tris(2,2'-bipyridyl)ruthenium(II)-complex (Ru(bpy)2+) to form a sandwich complex. After addition of streptavidin-coated microparticles, the complex becomes bound to the solid phase via interaction of biotin and streptavidin. The reaction mixture is then aspirated into the measuring cell where the microparticles are magnetically captured onto the surface of the electrode. Unbound substances are then removed with ProCell. Application of a voltage to the electrode induces chemiluminescent emission which is measured by a photomultiplier. Results are determined via a calibration curve which is instrument-specifically generated by 2-point calibration and a master curve provided via the reagent barcode.

Alternatively, an ImmunoCAP based assay (Phadia US, Inc.) may be used. In this assay, anti-IgE, covalently coupled to ImmunoCAP, reacts with the total IgE in the patient sample. After washing, enzyme labeled antibodies against IgE are added to form a complex. Following incubation, unbound enzyme-anti-IgE is washed away and the bound complex is then incubated with a developing agent. After stopping the reaction, the fluorescence of the eluate is measured. The fluorescence is directly proportional to the concentration of IgE in the sample. The higher the response, the more IgE is present in the sample. To evaluate the test results, the responses for the patient samples are transformed to concentrations with the use of a calibration curve.

A variety of patient samples may be used. Serum may be collected using standard sampling tubes or tubes containing separating gel, Li$^+$-heparin, Na$^+$-heparin, K$^+$-EDTA, and sodium citrate plasma. When sodium citrate is used, the results must be corrected by +10%.

References and citations to other documents, such as patents, patent applications, patent publications, journals, books, papers, web contents, have been made throughout this disclosure. All such documents are hereby incorporated herein by reference in their entirety for all purposes. Various modifications and equivalents of those described herein, will become apparent to those skilled in the art from the full contents of this document, including references to the scientific and patent literature cited herein. The subject matter herein contains information, exemplification and guidance that can be adapted to the practice of this disclosure in its various embodiments and equivalents thereof.

That which is claimed is:

1. A method of measuring biomarkers associated with non-coeliac gluten sensitivity (NCGS) in an individual suspected of having NCGS, comprising:
    obtaining a sample from the individual suspected of having NCGS; and
    measuring an established statistical difference from predetermined NCGS control values of an amount of interleukin 8 (IL-8), and at least one of interleukin 10 (IL-10), tumor necrosis factor alpha (TNF-Alpha) or total immunoglobulin E (IgE) in the sample obtained from the individual suspected of having NCGS,
    wherein the predetermined NCGS control values are amounts of IL-8, IL-10, TNF-Alpha, and total IgE found in individuals with no NCGS.

2. The method of claim 1, wherein the measuring comprises performing at least one immunoassay.

3. The method of claim 1, further comprising measuring expression of at least one of interferon gamma-induced protein 10 (IP-10), CD4 or CD45 in the sample obtained from the individual suspected of having NCGS relative to control expression value in the individuals with no NCGS.

4. The method of claim 3, wherein the measuring of the expression comprises performing flow cytometry.

5. The method of claim 1, wherein the sample comprises blood, serum, plasma or a tissue biopsy.

6. A method of measuring biomarkers associated with non-coeliac gluten sensitivity (NCGS) in an individual suspected of having NCGS, comprising:
    obtaining a sample from the individual suspected of having NCGS; and,
    measuring an established statistical difference from predetermined NCGS control values of expression of interleukin 8 (IL-8), and at least one of interleukin 10 (IL-10), tumor necrosis factor alpha (TNF-Alpha) or total immunoglobulin E (IgE) in the sample obtained from the individual suspected of having NCGS,
    wherein the predetermined NCGS control values are is IL-8, IL-10, TNF-alpha and total IgE expression found in individuals with no NCGS.

7. The method of claim 6, wherein the measuring comprises performing at least one immunoassay.

8. The method of claim 6, wherein the measuring comprises performing flow cytometry.

9. The method of claim 6, further comprising measuring expression of at least one of interferon gamma-induced protein 10 (IP-10), CD4 or CD45 in the sample obtained from the individual suspected of having NCGS relative to control expression value in the individuals with no NCGS.

10. The method of claim 6, wherein the sample comprises blood, serum, plasma or a tissue biopsy.

11. The method of claim 1, wherein the measuring comprises measuring amounts of IL-8 and IL-10 in the sample.

12. The method of claim 1, wherein the measuring comprises measuring amounts of IL-8 and TNF-Alpha in the sample.

13. The method of claim 1, wherein the measuring comprises measuring amounts of IL-8 and total IgE in the sample.

14. The method of claim 1, wherein the measuring comprises measuring amounts of IL-10 and TNF-Alpha in the sample.

15. The method of claim 1, wherein the measuring comprises measuring amounts of IL-10 and total IgE in the sample.

16. The method of claim 1, wherein the measuring comprises measuring amounts of TNF-Alpha and total IgE in the sample.

17. The method of claim 6, wherein the measuring comprises measuring expression of IL-8 and IL-10 in the sample.

18. The method of claim 6, wherein the measuring comprises measuring expression of IL-8 and TNF-Alpha in the sample.

19. The method of claim 6, wherein the measuring comprises measuring expression of IL-8 and total IgE in the sample.

20. The method of claim 6, wherein the measuring comprise measuring expression of IL-10 and TNF-Alpha in the sample.

21. The method of claim 6, wherein the measuring comprises measuring expression of IL-10 and total IgE in the sample.

22. The method of claim 6, wherein the measuring comprises measuring expression of TNF-Alpha and total IgE in the sample.

* * * * *

UNITED STATES PATENT AND TRADEMARK OFFICE
CERTIFICATE OF CORRECTION

PATENT NO.           : 11,125,759 B2
APPLICATION NO.      : 15/977173
DATED                : September 21, 2021
INVENTOR(S)          : Jessen et al.

It is certified that error appears in the above-identified patent and that said Letters Patent is hereby corrected as shown below:

In the Claims

In Column 32, Line 46, Claim 6: delete the word "is".

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*